(12) United States Patent
Arafat et al.

(10) Patent No.: US 7,524,516 B2
(45) Date of Patent: *Apr. 28, 2009

(54) CORROSION INHIBITING MILDEW REMOVER KIT

(75) Inventors: El Sayed S. Arafat, Leonardtown, MD (US); Raymond D. Rose, Great Mills, MD (US); Paul R. Roser, Leonardtown, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 29 days.

This patent is subject to a terminal disclaimer.

(21) Appl. No.: 11/345,686

(22) Filed: Jan. 26, 2006

(65) Prior Publication Data

US 2007/0172473 A1   Jul. 26, 2007

(51) Int. Cl.
*B65D 69/00* (2006.01)
*A01N 39/00* (2006.01)
*A01N 31/14* (2006.01)
*A01N 43/38* (2006.01)
*A01N 43/50* (2006.01)
*A01N 43/52* (2006.01)
*A01N 43/64* (2006.01)
*A01N 43/76* (2006.01)
*A01N 59/00* (2006.01)
*A01N 59/14* (2006.01)
*C11D 3/08* (2006.01)
*C11D 3/395* (2006.01)

(52) U.S. Cl. .............. 424/613; 206/223; 206/229; 206/568; 424/126; 424/615; 424/657; 424/722; 510/199; 510/334; 510/378; 510/421; 514/359; 514/375; 514/394; 514/396; 514/415; 514/717

(58) Field of Classification Search .............. 424/613, 424/724, 126, 615, 657, 722; 514/383, 375, 514/394, 359, 396, 415, 717; 210/223, 229, 210/568; 510/199, 334, 378, 421
See application file for complete search history.

(56) References Cited

U.S. PATENT DOCUMENTS

| 4,321,166 | A  | * | 3/1982 | McGrady ................ 510/335 |
| 5,480,576 | A  | * | 1/1996 | Gary et al. ................ 510/220 |
| 5,698,504 | A  | * | 12/1997 | Christie et al. ............. 510/220 |
| 6,235,124 | B1 | * | 5/2001 | Rubin ..................... 134/26 |
| 6,454,819 | B1 | * | 9/2002 | Yano et al. ................ 51/298 |
| 6,655,527 | B1 | * | 12/2003 | Rubin ..................... 206/229 |
| 6,818,313 | B2 | * | 11/2004 | Phelps et al. .............. 428/457 |
| 7,001,605 | B2 | * | 2/2006 | Matsuo et al. ............. 424/405 |
| 2004/0203324 | A1 | * | 10/2004 | Smith et al. ................ 451/41 |

OTHER PUBLICATIONS

U.S. Appl. No. 11/151,170, filed Jun. 10, 2005, El Sayed S. Arafat.

* cited by examiner

*Primary Examiner*—John Pak
*Assistant Examiner*—Nathan W Schlientz
(74) *Attorney, Agent, or Firm*—Mark O. Glut

(57) ABSTRACT

The corrosion inhibiting mildew remover kit includes a premeasured amount of sodium perborate, a premeasured amount of a liquid inhibitor and a premeasured amount of a liquid blend. The premeasured amount of sodium perborate, the premeasured amount of liquid inhibitor, the premeasured amount of liquid blend and water combine to form an aqueous solution that can be applied to a mildew infected area. The aqueous solution removes mildew from a mildew infected area and does not cause corrosion.

12 Claims, 1 Drawing Sheet

CORROSION INHIBITING MILDEW REMOVER KIT

STATEMENT OF GOVERNMENT INTEREST

The invention described herein may be manufactured and used by or for the Government of the United States of America for governmental purposes without payment of any royalties thereon or therefor.

CROSS-REFERENCE TO RELATED APPLICATIONS

The above listed invention is hereby cross-referenced and related to U.S. patent application Ser. No. 11/151,170 filed Jun. 10, 2005, entitled "Composition and Process for Removing and Preventing Mildew and Fungal Growth" by inventors El Sayed S. Arafat, Craig A. Matzdorf, Stephen Spadafora, David Gauntt, Paul Roser, and James Whitfield. U.S. patent application Ser. No. 11/151,170 is not admitted to be prior art with respect to the present invention. The patent application is hereby incorporated by reference. Both inventions are assigned to the same assignee.

BACKGROUND

The present invention relates to a corrosion inhibiting mildew remover kit. More specifically, but without limitation, the present invention relates to a kit that removes mildew from aircraft and is also a corrosion inhibitor.

The damaging effects of mildew are well known throughout the scientific and non-scientific community. Mildew growth on interior surfaces of aircraft, particularly military aircraft, has been a chronic problem, especially when these aircraft are operated in humid climates. Excess buildup of mildew can cause corrosion as well as operational damage to aircraft. Mildew can also cause accelerated degradation of paint and decals. Mildew buildup is also a health hazard to pilots and maintenance personnel. Buildup of mildew causes unpleasant odors and can be demoralizing to pilots, maintenance personnel and passengers.

Most methods of mildew removal have proven to be extremely time consuming, labor intensive and often inadequate. Solutions that adequately removed mildew in the past have caused accelerated corrosion to the aircraft structural metals as well as to the aircraft. Other solutions, such as ones containing sodium hypochlorite (chlorine bleach), are damaging to the environment and metal surfaces. Certain solutions require many ingredients, which are difficult, potentially dangerous, and time consuming to prepare and use. Other solutions are expensive as well as difficult and dangerous to store.

U.S. Pat. No. 6,235,124 (Method and Solution for Removal of Mildew by Lynn Rubin, issued May 22, 2001) teaches the user the method to prepare an aqueous solution with sodium perborate and a non-ionic detergent. Testing has found that once this solution is prepared it is no longer an effective mildew remover after 24 hours. Therefore, the solution must be prepared and then used as soon as possible. Thus there existed the need for a system or a kit for preparing the solution and then immediately applying the solution to a mildew infected area. U.S. Pat. No. 6,655,527 (Kit for Removing Mildew by Lynn Rubin, issued Dec. 2, 2003) claims a kit for preparing the solution and immediately applying the solution to a mildew-infected area. Testing has shown the mildew remover and kit of these patents are not adequately corrosion-inhibiting. The mildew remover and kit failed certain test requirements for corrosion resistance. The test requirements are described in MIL-PRF-85570D (Cleaning Compound, Aircraft Exterior, dated 19 Jun. 2002) and ADS-61A-PRF-2002 (Aeronautical Design Standard Performance Specification Cleaners, Aqueous and Solvent, for Army Aircraft) specifications. The MIL-PRF-85570D and ADS-61A-PRF-2002 specifications are hereby incorporated by reference. U.S. Pat. Nos. 6,235,124 and 6,655,527 and the MIL-PRF-85570D and ADS-61A-PRF-2002 specifications are not admitted to be prior art with respect to the present invention.

A corrosion-inhibited version of the mildew remover described in U.S. Pat. Nos. 6,235,124 and 6,655,527 has been invented and described in U.S. patent application Ser. No. 11/151,170 filed Jun. 10, 2005.

There is also a need for a corrosion inhibiting mildew remover kit wherein the cleaning solution may be simply prepared in a non-laboratory environment, such as on an airfield, a factory, a yard or aboard a ship, and prepared by an unskilled laborer, layperson or an apprentice sailor, soldier or airman easily and quickly.

For the foregoing reasons, there is a need for a kit for removing mildew and does not cause corrosion.

SUMMARY

The present invention is directed to a corrosion inhibiting mildew remover kit that meets the needs enumerated above and below.

The present invention is directed to a corrosion inhibiting mildew remover kit, which includes a premeasured amount of sodium perborate, a premeasured amount of a liquid blend and a premeasured amount of liquid inhibitor. The premeasured amount of sodium perborate, the premeasured amount of liquid blend, the premeasured amount of liquid inhibitor and water combine to form an aqueous solution that can be applied to a mildew infected area. Upon application, the aqueous solution removes mildew from a mildew infected area within about 5 to 15 minutes, and does not cause corrosion.

It is also a feature of the invention to provide for a corrosion inhibiting mildew remover kit wherein the mildew removing/corrosion inhibitor solution may be simply prepared in a non-laboratory environment, and prepared by an unskilled laborer or an apprentice sailor, soldier or airman easily and quickly.

It is a feature of the present invention to provide a corrosion inhibiting mildew remover kit that is inexpensive, easy to store and environmentally friendly. Sodium perborate is a free flowing granular chemical that is easy to store and use. Ninety-six hours after mixing with water, the resultant solution of sodium perborate decomposes into water, oxygen and sodium borate.

It is also a feature of the invention to provide a corrosion inhibiting mildew remover kit that utilizes a mildew removing system that is non-corrosive to aluminum, steel and aircraft structural materials. The resultant solution inhibits corrosion by passivating metal surfaces and increasing the life of various materials. The solution and method removes and also delays the growth of mildew on aircraft. The kit for removing mildew may also be used to effectively remove mildew from cars, trucks, trains, ships, buildings or any other object that needs removal of mildew.

It is a further feature of the invention to provide a corrosion inhibiting mildew remover kit, which provides mildew removal, bleaching, and stain removal. The resultant solution also works to enhance removal of common operational oils and soils as well as the removal of mildew.

It is also a feature of the present invention to provide a corrosion inhibiting mildew remover kit, wherein the resultant solution breaks down protein channels within the fungus (mildew), thus eliminating its presence, not just bleaching the stain.

It is also a feature of the invention to reduce cleaning time of aircraft. Current methods require significant cleaning time and can cause delays in having the aircraft available for use. The present invention has been shown to decrease cleaning time.

These and other features, aspects and advantages of the present invention will become better understood with reference to the following description and appended claims.

BRIEF DESCRIPTION OF THE DRAWINGS

These and other features, aspects and advantages of the present invention will become better understood with reference to the following description and appended claims, and accompanying drawing wherein:

DESCRIPTION

Figure 1:
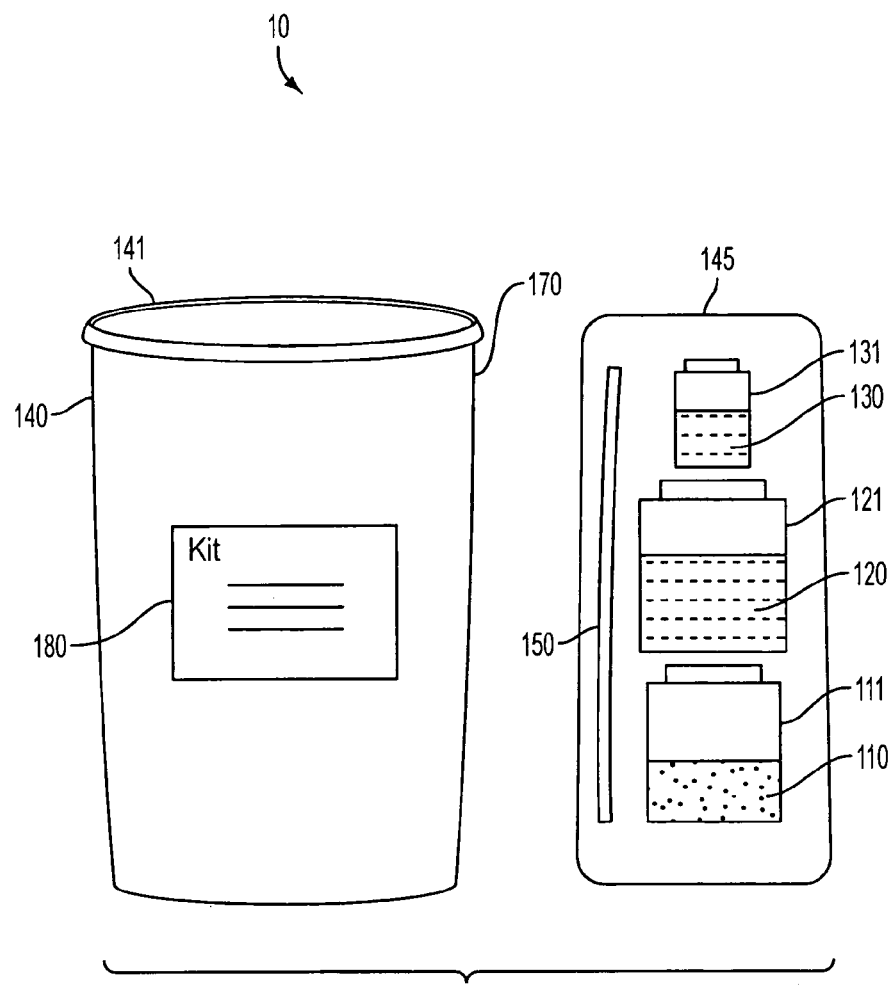
FIG. 1 is a perspective view of one of the preferred embodiments of the corrosion inhibiting mildew remover kit.

One of the preferred embodiments of the present invention is illustrated by way of example in FIG. 1. As shown in FIG. 1, the corrosion inhibiting mildew remover kit 10 includes a premeasured amount of sodium perborate 110, a premeasured amount of a liquid blend 120, and a premeasured amount of a liquid inhibitor 130.

The premeasured amount of sodium perborate 110 may be stored in a sodium perborate container 111. A container may be defined, but without limitation, as anything that can contain or hold something, a compartment, a receptacle, a carton, a box, a bag, or any apparatus that can store something and prevent it from spilling or falling out of the apparatus. A container typically may have a cap or opening to allow the contents to be poured out or removed from the container. The sodium perborate 110 may be stored in any type of container that may be manufactured from, but without limitation, plastic, or any type of material that lends itself to the manufacture of a container that would safely and effectively store sodium perborate 110. The preferred sodium perborate container 111 is an openable sealed plastic bottle that is appropriately labeled. The premeasured amount of sodium perborate 110 may be in powder form. In the preferred embodiment of the invention, about 270 to about 310 grams of sodium perborate may be disposed within a 500 ml container.

The liquid blend 120 can be any non-ionic cleaner or non-ionic detergent alone, or a combination of an inhibitor and a non-ionic cleaner/detergent. The premeasured amount of liquid blend 120 may be stored in a detergent container 121. The detergent container 121 may be manufactured from, but without limitation, plastic, or any type of material that lends itself to the manufacture of a container that would safely and effectively store a liquid blend. The preferred detergent container 121 is an openable sealed plastic bottle that is appropriately labeled.

The premeasured amount of liquid blend 120 can be an inhibitor mixed with any detergent conforming to military specification MIL-D-16791G (incorporated herein by reference) or the equivalent. The non-ionic detergent can be in liquid form, and a non-ionic surface-active agent containing a minimum of 99% active ingredient. Some examples, but without limitation, of the types of detergents that can be used are alkyl aryl polyether alcohol (alkyl phenol ether of poly-ethylene glycol) type where the alkyl group is iso-octyl or isononyl, or the linear alkyl polyether alcohol (alkyl ether of polyethylene glycol) type where the alkyl group is linear primary or secondary alkyl. However, any type of naturally occurring or synthetic detergents or surfactants can be used. The preferred liquid blend 120 is prepared by heating distilled water to approximately 120° F., then adding a non-ionic detergent to the heated water, mixing the water and the non-ionic detergent, then adding benzotriazole, and mixing the resultant solution. In the preferred embodiment, about 900 ml of distilled water is heated, about 60 to about 90 grams of non-ionic detergent is added to the water and mixed for about 2 minutes, about 40 to about 60 grams of benzotriazole is mixed with the water and non-ionic detergent solution for about 30 minutes. In the preferred embodiment of the invention, the detergent container 121 is a 1000 ml plastic bottle, with the liquid blend 120 disposed within the detergent container 121.

The liquid inhibitor 130 may be any type of chemical that arrests a chemical action or a compound that produces an invisible protective film on a metal or metal alloy article. The preferred liquid inhibitor 130 is sodium silicate. The premeasured amount of liquid inhibitor 130 may be stored in an inhibitor container 131. The inhibitor container 131 may be manufactured from, but without limitation, plastic, metal, metal alloy, aluminum foil, or any type of material that lends itself to the manufacture of a container that would safely and effectively store a liquid inhibitor. The preferred inhibitor container 131 is an openable sealed plastic bottle that is appropriately labeled. In the preferred embodiment of the invention, the inhibitor container 131 is a 125 ml plastic container with about 80 to about 110 grams of liquid sodium silicate disposed within the inhibitor container 131.

The corrosion inhibiting mildew remover kit 10 may also contain a mixing container 140 for mixing the premeasured amount of sodium perborate 110, the premeasured amount of liquid blend 120, the premeasured amount of liquid inhibitor 130 and water. The mixing container 140 may be a large open ended or partially open ended container, drum, bottle, tank, jug, carboy, can, tub, pail, urn, jar, or the like. The mixing container 140 may have a cap or lid to cover the opening. When the sodium perborate 110, the liquid blend 120, the inhibitor 130 and water are mixed they form an aqueous solution that can effectively clean and remove mildew.

The corrosion inhibiting mildew remover kit 10 may also include a storage sleeve 145. The premeasured amount of sodium perborate 110, liquid blend 120 and inhibitor 130 (disposed within their respective containers) may be stored in the storage sleeve 145. In the preferred embodiment, as seen in FIG. 1, each respective container (111, 121, 131) may be stacked within the storage sleeve 145. The storage sleeve 145 may be vacuumed and heat sealed.

The corrosion inhibiting mildew remover kit 10 may also include an agitator 150 to mix and agitate the solution. An agitator 150 is any device, system or apparatus that can shake, mix or move the ingredients briskly. The agitator 150 could be, but without limitation, a large spoon, ladle, scoop, mixer, stirrer, dipper, stick or the like. If the mixing container 140 has a lid, the mixing container 140 (with the prepared aqueous solution within the mixing container 140) can be shaken to properly agitate the aqueous solution. In the preferred embodiment, a stir stick may be used as an agitator 150. The stir stick may be disposed within the storage sleeve 145.

The agitator 150 may be an automated agitator utilizing mechanical and/or electrical devices to properly agitate the aqueous solution. The agitator 150 may be, but without limitation, an automatic fan stirrer, an automated shaker, a robot agitator, a drill with an agitation bit attached, or the like. The agitator 150 may also be, but without limitation, an air-powered mixer, an electric mixer, a direct drive mixer, a gear drive mixer, a single propeller mixer, a dual propeller mixer, or any other type of agitator or mixer. It is understood, however, any type of mechanical, electrical, or any combination thereof, agitator or agitation process can be utilized where practicable.

The corrosion inhibiting mildew remover kit 10 may also contain a solution applicator. The solution applicator is any device, system or apparatus that can apply the mixed aqueous solution to a mildew infected area. The solution applicator can be an applicator, but without limitation, selected from the group of a spray bottle, a chemical wash bottle with a dispensing nozzle, a compression sprayer, a conventional sprayer, a nylon brush and cheesecloth. When using a spray bottle the solution may be poured into the spray bottle and sprayed on the mildew-infected area. The applicator may be a drum or pail pump or dispensing and transferring the aqueous solution from the mixing container 140 onto the mildew infected area.

The corrosion inhibiting mildew remover kit 10 may also include a kit container 170. The kit container 170 can be a housing that can hold or store all the items of the kit 10. Within the kit container 170 there may be component fasteners, which fasten each item of the kit for removing mildew 10 to the inside of the kit container 170. In one of the embodiments, as seen in FIG. 1, the mixing container 140 may also serve as the kit container 170. All the items would be placed in the mixing container 140 and the mixing container 140 may contain a lid 141 in order to keep all the items safely stored inside the mixing container 140 during transport or storage of the kit 10.

The kit 10 can also include a set of instructions 180 on how to use the kit 10 to remove mildew from a mildew infected area. These instructions 180 could include the method described in U.S. patent application Ser. No. 11/151,170. Specifically, the preferred instructions for a preferred embodiment of the invention could state: (1) fill a container with about five gallons of water; (2) add the premeasured amount of liquid inhibitor into the water and mix thoroughly with the stir stick; (3) shake the premeasured amount of liquid blend vigorously for about 30 seconds; (4) add the premeasured amount of liquid blend to the solution and mix thoroughly with the stir stick; (5) add the premeasured amount of sodium perborate into the solution and dissolve by agitating thoroughly; (6) apply the solution to a mildew infected area and allow to remain on surface for about 5 to 15 minutes; (7) scrub infected area and thoroughly rinse treated surfaces with water; (8) reapply as necessary until all residue is removed.

The corrosion-inhibiting mildew remover kit of the present invention can consist essentially of a premeasured amount of an alkali metal perborate stored in a container; a premeasured amount of a liquid blend consisting essentially of a surfactant and benzotriazole and/or tolyltriazole stored in a container; and a premeasured amount of an alkali metal silicate stored in a container; wherein at the time of use said premeasured amount of the perborate, said premeasured amount of the liquid blend, and said premeasured amount of the silicate are combined with a premeasured amount of water to form an aqueous solution consisting essentially of:
  (a) from about 0.1 to 3.0 percent by weight of at least one alkali metal perborate;
  (b) from about 0.05 to 5.0 percent by weight of at least one alkali metal silicate;
  (c) benzotriazole, tolyltriazole, or a mixture thereof; and
  (d) 0.1 to 5.0 percent by weight of at least one water soluble surfactant;

wherein the composition has a pH ranging from 7.0 to 10, does not include a chlorine bleach, and the combined amount of ingredients (b) and (c) does not exceed about 5.0 weight percent of the composition.

The corrosion-inhibiting mildew remover kit of the present invention can also consist essentially of a premeasured amount of powdered sodium perborate stored in a container; a premeasured amount of sodium silicate stored in a container; a premeasured amount of a liquid blend consisting of benzotriazole and tolyltriazole and a premeasured amount of surfactant selected from the group consisting of alkylaryl polyether alcohols, and alkyl polyether alcohols stored in a container; and a container with an agitator for mixing said ingredients; wherein at the time of use said premeasured amount of the sodium perborate, said premeasured amount of the sodium silicate, said premeasured amount of the liquid blend, and said premeasured amount of surfactant are combined with a premeasured amount of water to form an aqueous solution consisting essentially of:
  (a) from about 0.1 to 3.0 percent by weight of sodium perborate;
  (b) from about 0.05 to 5.0 percent by weight of sodium silicate;
  (c) benzotriazole and tolyltriazole; and
  (d) 0.1 to 5.0 percent by weight of said surfactant;

wherein the composition has a pH ranging from 7.0 to 10, does not include a chlorine bleach, and the combined amount of sodium silicate, benzotriazole, and tolyltriazole does not exceed about 5.0 weight percent of the composition.

When introducing elements of the present invention or the preferred embodiment(s) thereof, the articles "a", "an", "the" and "said" are intended to mean there are one or more of the elements. The terms "comprising," "including," and "having" are intended to be inclusive and mean that there may be additional elements other than the listed elements.

This invention further relates to a kit comprising compositions and to the process of using the compositions for removing and preventing mold, mildew and fungal growth on various surfaces. The composition comprises an aqueous solution having a pH ranging from 7.0 to 10 and contains from about 0.1 to 3.0 percent by weight of at least one alkali metal perborate, from about 0.05 to 5.0 percent by weight of one or more inhibiting compound selected from the group consisting of alkali metal silicates, triazoles such as benzotriazole and mixtures of said silicates and triazoles in any ratio. In addition, the aqueous solutions contain from about 0.0 to 3.0 percent by weight of at least one water soluble corrosion inhibitor selected from the group consisting of benzimidazoles, benzazoles and benzoxazoles, and from about 0.0 to 5.0 percent by weight of at least one water soluble surfactant.

Table 3 details the combination of inhibitors investigated and the subsequent sandwich corrosion test results. The test results are shown in Tables 1 and 2. The original mildew remover showed surface corrosion and pitting corrosion on all coupons except anodized 7075-T6 (250/12). The distilled water did not show any corrosion on aluminum coupons, except for some staining which appeared on the anodized 2024-T3 (250/4) coupons. The test was performed twice with Whatman filter paper #4 and once with Whatman Glass Microfiber. Overall performance is detailed as follows:

The original mildew remover formulation (Example 1) failed the sandwich corrosion test, as required by the MIL-PRF-85570D and ADS 61A-PRF-2002 specifications as follows:

a. Dilutions of the original mildew remover (50%, 25% and 10% concentration) proved corrosive beyond the specification limits and pitting was observed.

b. Samples made using 24-hour-old solution (uninhibited formula) were found to fail sandwich corrosion testing.

c. Samples made using 96-hour-old solution (uninhibited formula) were found to be comparable to the control.

d. Samples tested at the prescribed temperature of 100° F. showed more pitting than those tested at 72° F.

e. Samples made using tap water in place of reagent water failed with ratings of #4 for corrosion pitting.

The mildew remover formulation (Example 2) passed the sandwich corrosion test, in accordance with the MIL-PRF-85570D and ADS-61A-PRF-2002 specification requirements.

The following examples illustrate the aqueous solutions of this invention, and the method of using the basic solutions for removing and inhibiting the growth of mold and mildew on various surfaces and particularly metal surfaces.

EXAMPLE 1

The original Mildew Remover (M.R.) Formulation (uninhibited) consists of the following compounds in an aqueous solution:
Sodium Perborate Monohydrate, 1.5% by weight
Triton X-100 surfactant, 0.39% by weight
Reagent Water (ASTM D1193)

EXAMPLE 2

Inhibited Mildew Remover (M.R.) consists of the following compounds in an aqueous solution:
Sodium Perborate Monohydrate, 1.5% by weight
Triton X-100 surfactant, 0.39% by weight (octylphenoxypolyethoxyethanol)
Sodium Silicate N, 0.5% by weight
Benzotriazole, 0.25% by weight
Reagent Water (ASTM D1193)

EXAMPLE 3

Inhibited Mildew Remover consists of the following compounds in solution:
Sodium Perborate Monohydrate, 1.5% by weight
Triton X-100 surfactant, 0.39% by weight (octylphenoxypolyethoxyethanol)
Sodium Silicate N, 0.5% by weight
2-Mercaptobenzimidazole, 0.25% by weight
Reagent Water (ASTM D1193)

EXAMPLE 4

| Aqueous Compositions | Percent by Weight |
|---|---|
| Alkali Metal Perborates | 0.1 to 3.0 |
| (Sodium and/or Potassium Perborates) | 1.0 to 2.0 |
| Inhibiting compounds | 0.05 to 5.0 |
| (Silicates and triazoles) | 0.1 to 2.0 |
| Corrosion Inhibitors | 0.0 to 3.0 |
| (Benzimidazoles, benzazoles, benzoxazoles) | 0.1 to 2.0 |
| Surfactants | 0.0 to 5.0 |
| (non-ionic, cationic, anionic) | 0.1 to 2.0 |

Total Immersion Corrosion Test: The total immersion corrosion test was performed in accordance with ASTM F483. The selected metal alloys were immersed in the mildew remover solution for seven days at 100° F. The weight change of each specimen was calculated, and the specimen was examined for visual evidence of corrosion. The weight changes for the selected metal alloys are listed in Table 1. The selected metal alloys met the test requirements except the Ti 6Al 4V alloy which showed a dark purple color. This dark purple color is an indication of the oxidation of vanadium in the alloy to vanadium oxide. The inhibited mildew remover formulas of Example 2 and 3 did not yield the dark purple color on titanium and met the requirements of the total immersion corrosion test. Various inhibitors for the mildew remover were tested that did not achieve the optimum result or were not environmentally acceptable, see Table 3. Sandwich Corrosion testing was performed using diluted chlorine bleach solution, Reagent Water (ASTM D1193), Synthetic Tap Water (MIL-C-85570), a 1.5% sodium perborate solution, and a series of perborate and surfactant solutions with various corrosion inhibitors in several concentrations. Inhibitors tested include Zinc Borate, Sodium Dichromate, Monacor 4000, Benzotriazole, Sodium Silicate "N", Sodium Benzoate, Sodium Orthosilicate, Sodium Metasilicate, Cobratec TT-50-S, Sodium Nitrite, 2-Mercaptobenzimidazole, and 2-Mercaptobenzoxazole. Table 3 details the combination of inhibitors investigated and the subsequent sandwich corrosion test results. Screening of the inhibitors showed that various combinations worked for some substrates, but only the formulation of Examples 2 and 3 passed both the MIL-PRF-85570D and ADS-61-A-PRF-2002 requirements of having no rating greater than #1 or no greater than the control rating in the sandwich corrosion test as shown in Table 3.

The alkali metal perborates of this invention and preferably the sodium and potassium perborates are added to the aqueous solutions in amounts ranging from about 0.1 to 3.0 percent by weight and preferably in amounts ranging from about 1.0 to 2.0 percent by weight of the solutions. To obtain maximum performance in preventing and removing mold and mildew growth on metal surfaces such as aluminum, the inhibiting compounds i.e. the alkali metal silicates such as sodium and potassium silicates and the triazoles are added to the aqueous solution in amounts ranging from about 0.05 to 5.0 percent and preferably in amounts ranging from about 0.1 to 2.0 percent by weight of the solution. These inhibiting compounds are selected from the group consisting of alkali metal silicates and triazoles such as benzotriazole or tolyltriazole and various mixtures of said silicates and triazoles in any ratio.

In preparing the anti-mildew or inhibiting solutions of this invention, known water soluble surfactants are added to the solutions in amounts ranging from about 0.0 to 5.0 percent by weight and preferably from 0.1 to 2.0 or from about 0.1 to 1.0 percent by weight. The surfactants are added to the aqueous solution to provide better wetting properties by lowering the surface tension thereby insuring complete coverage and a more uniform film on the metal substrates. The surfactants include at least one water soluble compound selected from the group consisting of non-ionic, anionic, and cationic surfactants. Some of the water soluble surfactants include monocarboxylimidoazoline, alkylsulfate sodium salts (DUPONOL®), salts of alkylbenzene sulfonates, ethoxylated or propoxylated alkylphenols (IGEPAL®), alkylsulfonamides, alkaryl sulfonates, palmiticalkanol amides (CENTROL®), the alkylarylpolyether alcohols such as octylphenylpolyethoxy ethanol or polyoxyethylene nonylphenyl ether, (TRITON®), sorbitan monopalmitate (SPAN®), dodecylphenyl polyethyleneglycol ether (TERGITOL®), alkyl pyrrolidones, polyalkoxylated fatty acid esters, lower alkylbenzene sulfonates and various mixtures of these surfactants.

The preferred corrosion inhibitors added to the solutions of this invention are water-soluble compounds selected from the group consisting of benzimidazoles, benzazoles, benzoxazoles and mixtures of these corrosion inhibitors in any ratio. The corrosion inhibitors are dissolved in the aqueous solutions, having a pH ranging from 7.0 to 10, in amounts ranging from about 0.0 to 3.0 percent by weight and preferably in amounts ranging from about 0.1 to 2.0 percent by weight of the solution. The preferred inhibitor compounds in addition to the silicates include triazoles containing up to 12 carbon atoms. The preferred aryl triazoles contain from 6-10 carbon atoms, including compounds such as benzotriazole and tolyltriazole. The aryl triazoles are commercially available under the trade name "COBRATEC".

An embodiment of the anti-mildew or inhibiting solution consists essentially of an aqueous solution of from about 1.0 to 2.0 percent by weight of at least one alkali metal perborate; from about 0.1 to 2.0 percent by weight of at least one alkali metal silicate; a member selected from the group consisting of (i) benzotriazole, tolyltriazole, or a mixture thereof, and (ii) from about 0.1 to 2.0 weight percent of at least one water soluble corrosion inhibitor selected from the group consisting of benzimidazoles, benzazoles, and benzoxazoles; and 0.1 to 2.0 percent by weight of at least one water soluble surfactant; wherein the composition has a pH ranging from 7.0 to 10, does not include a chlorine bleach, and when benzotriazole, tolyltriazole, or a mixture thereof is present in the composition the combined amount of alkali metal silicate and benzotriazole, tolyltriazole, or a mixture thereof is from about 0.1 to 2.0 percent by weight.

As shown, a combination of inhibitors e.g. silicates and triazoles was developed to eliminate the corrosion problems associated with the original (Example 1) mildew remover formula. The inhibited mildew remover formula eliminates the corrosion problem associated with aluminum alloys in the sandwich corrosion test. In addition, the inhibited mildew remover formula eliminated the problem associated with titanium alloys in the total immersion corrosion test. The inhibited mildew remover formula also protects against potential damage caused by the oxidative effect of the uninhibited formula on aircraft metals. These factors were taken in consideration with all other precautions normally taken to minimize the damage potential of the instant composition in the Standard Depot Level Maintenance (SDLM) procedures. The cleaning efficiency test results were satisfactory on both the original and inhibited formulations.

Although the present invention has been described in considerable detail with reference to a certain preferred embodiment thereof, other embodiments are possible. Therefore, the spirit and scope of the appended claims should not be limited to the description of the preferred embodiment(s) contained herein.

Table 1 is an evaluation of the uninhibited and inhibited mildew remover in accordance with MIL-PRF-85570D (Cleaning Compounds, Aircraft Exterior).

TABLE 1

| Requirements | Specification Limits | Uninhibited Mildew Remover | Inhibited Mildew Remover |
|---|---|---|---|
| pH (ASTM E70) | 7-10 | 10.31-10.48 | 9.98 |
| Sandwich Corrosion Test (ASTM F1110) | Not more than distilled water | Failed Al 250/5 Al 250/13 Al 250/4 | Pass |
| Total Immersion Corrosion Test (ASTM F483) | No Visible Corrosion mg/cm$^2$/day Al 7075 (250/12) 0.04 Steel 1020 (AMS 5046) 0.04 Ti 6Al 4V (AMS 9046) 0.04 Mg AZ31B (AMS4377) 0.20 | Mg/cm$^2$/day <0.01 <0.01 <0.01 Purple Color 0.02 | Mg/cm$^2$/day <0.01 <0.01 <0.01 0.02 |
| Cadmium Corrosion (ASTM F1111) | Mg/cm$^2$/day 0.20 | <0.01 | <0.01 |
| Hydrogen Embrittlement (ASTM F519 1a) | No Failure to 150 hr when loaded at 45% | Pass | Pass |
| Effect on Plastics (ASTM F484) | Acrylic Type A No Crazing—8 hrs | Pass | Pass |
| | Acrylic Type C No Crazing—8 hrs | Pass | Pass |
| | Polycarbonate MIL-P-83310—2 hrs | Pass | Pass |
| Effect on Painted Surfaces (ASTM F502) | No Softening > 1 Pencil Hardness | Pass | Pass |
| Effect on Polyimide Wire | No Dielectric Leakage No Physical Effect > Dist. Water | Pass | Pass |

Table 2 shows the evaluation of uninhibited and inhibited mildew remover in accordance with ADS-61A-PRF-2002 (Army Aircraft Cleaner).

TABLE 2

| Requirement | Specification Limits | Uninhibited Mildew Remover | Inhibited Mildew Remover |
|---|---|---|---|
| Sandwich Corrosion Test (ASTM F1110) | Not more than distilled water | Failed Al 250/5 Al 250/13 | Pass Al 250/4 |
| Total Immersion Corrosion Test (ASTM F483) | No Visible Corrosion mg/cm$^2$/168 hr Al 7075 (250/12) 0.49 Steel 1020 (AMS 5046) 0.49 Ti 6Al 4V (AMS 9046) 0.35 Mg AZ31B (AMS4377) 0.70 | Pass Except Titanium (Per Table 1) | Pass |
| Stress Corrosion | No Cracks in Table II Metals | Pass | Pass |
| Hydrogen Embrittlement (ASTM F519 1a) | No Failure to 150 hr when loaded at 45% | Pass | Pass |
| Effect on Plastics (ASTM F484) | Acrylic Type A No Crazing—8 hrs | Pass | Pass |
| | Acrylic Type C No Crazing—8 hrs | Pass | Pass |
| | Polycarbonate MIL-P-83310—2 hrs | | Pass |

TABLE 2-continued

| Requirement | Specification Limits | Uninhibited Mildew Remover | Inhibited Mildew Remover |
|---|---|---|---|
| Effect on Painted Surfaces (ASTM F502) | No Softening > 1 Pencil Hardness | Pass | Pass |
| Effect on Polyimide Wire | No Dielectric Leakage No Physical Effect > Dist. Water | Pass | Pass |
| Sealant Adhesions | 100% Cohesive Failure 3.5 kN/m | Primer Conforms Topcoat | Primer Conforms Topcoat |
| Adhesive Bonding | Meet or Exceed Control Methylethyl ketone | Failed Control and Cleaner Primer Conforms Topcoat Failed Control and Cleaner | Failed Control and Cleaner Primer Conforms Topcoat Failed Control and Cleaner |

TABLE 3

ASTM F1110-02 Sandwich Corrosion Test Ratings

| Formula Number | Formulation | 250/4 Anodized | 250/5 Clad | 250/12 Anodized | 250/13 Clad |
|---|---|---|---|---|---|
| Control | Reagent Water | 1-2 | 1 | 1 | 1 |
| Formula #1 | Standard Formulation (Example 1) | 3-4 | 3-4 | 0-1 | 4 |
| Formula #2 | Standard Formula Plus 0.1% Zinc Borate | 2 | 1-2 | 1 | 3-4 |
| Formula #3 | Standard Formula Plus 0.1% Sodium Dichromate | 1 | 1 | 1 | 1 |
| Formula #4 | Standard Formula Plus 0.2% Sodium Dichromate | 1 | 1 | 1 | NR |
| Formula #5 | Standard Formula Plus 0.1% Benzotriazole | 1 | 1 | 1 | 2 |
| Formula #6 | Standard Formula Plus 0.25% N Sodium Silicate | 1-2 | 1-2 | 1 | 1 |
| Formula #7 | Standard Formula Plus 0.5% N Sodium Silicate | 1 | 1 | 1 | NR |
| Formula #8 | Standard Formula Diluted to 10% Concentration | 1 | NR | 4 | 3-4 |
| Formula #9 | Standard Formulation Diluted to 25% Concentration | 1-2 | 2 | 2 | 1-2 |
| Formula #10 | Standard Formulation Diluted to 50% Concentration | 1 | 2 | 1 | 2-3 |
| Formula #11 | Standard Formula Plus 0.25% Sodium Benzoate | 1 | 2 | 1 | NR |
| Formula #12 | Standard Formula Plus 0.5% Sodium Benzoate | 1-2 | 2-4 | 1 | 2-4 |
| Formula #13 | Standard Formula Plus 0.25% Sodium Orthosilicate | 4 | 2-3 | 4 | NR |
| Formula #14 | Standard Formula Plus 0.25% Sodium Metasilicate | 1-2 | 4 | 1-2 | NR |
| Formula #15 | Standard Formula Plus 1.0% Monacor 4000 | 1 | 3-4 | 1 | 4 |
| Formula #16 | Standard Formula Plus 0.25% Cobratec TT-50-S | 0-1 | 0-2 | 1-3 | 2-4 |
| Formula #17 | Standard Formula Plus 0.25% Monacor 4000 + 0.25% N Sodium Silicate | 4 | 1-4 | 1 | 1-4 |
| Formula #18 | Standard Formula Plus 0.5% Monacore 4000 + 0.25% N Sodium Silicate | 4 | 1 | 4 | 1 |
| Formula #19 | Standard Formula Plus 0.5% Monacore 4000 + 0.5% N Sodium Silicate | 3 | 1 | 3 | 1 |
| Formula #20 | Standard Formula diluted to 10% concentrate in Tap Water | 1 | NR | 4 | 2 |
| Formula #21 | Standard Formula Plus 0.5% N Sodium Silicate + 0.25% Benzotriazole | 1 | 1 | 0 | 1 |
| Formula #22 | Standard Formula Plus 0.5% N Sodium Silicate + 0.25% 2-mercaptobenzimidazole | 1 | 1 | 0 | 1 |
| Formula #23 | Standard Formula Plus 0.5% N Sodium Silicate + 0.25% 2-mercaptobenzoxazole | 4 | 1 | 1 | 1 |

TABLE 3-continued

ASTM F1110-02 Sandwich Corrosion Test Ratings

| Formula Number | Formulation | 250/4 Anodized | 250/5 Clad | 250/12 Anodized | 250/13 Clad |
|---|---|---|---|---|---|
| Formula #24 | Standard Formula Plus 0.25% Sodium Nitrite | 1-2 | 1-2 | 1 | 3 |

0 - No Visible Corrosion
1 - Very Slight Corrosion or Discoloration (up to 5% of surface area)
2 - Slight Corrosion (5 to 10%)
3 - Moderate Corrosion or Pitting (10 to 25%)
4 - Extensive Corrosion or Pitting (25% or more)
* NR: Not Run

What is claimed is:

1. A corrosion-inhibiting mildew remover kit consisting essentially of a premeasured amount of an alkali metal perborate stored in a container; a premeasured amount of a liquid blend consisting essentially of a surfactant and benzotriazole and/or tolyltriazole stored in a container; and a premeasured amount of an alkali metal silicate stored in a container; wherein at the time of use said premeasured amount of the perborate, said premeasured amount of the liquid blend, and said premeasured amount of the silicate are combined with a premeasured amount of water to form an aqueous solution consisting essentially of:
   (a) from about 0.1 to 3.0 percent by weight of at least one alkali metal perborate;
   (b) from about 0.05 to 5.0 percent by weight of at least one alkali metal silicate;
   (c) benzotriazole, tolyltriazole, or a mixture thereof; and
   (d) 0.1 to 5.0 percent by weight of at least one water soluble surfactant;
wherein the composition has a pH ranging from 7.0 to 10, does not include a chlorine bleach, and the combined amount of ingredients (b) and (c) does not exceed about 5.0 weight percent of the composition.

2. A corrosion-inhibiting mildew remover kit consisting essentially of a premeasured amount of sodium perborate stored in a container; a premeasured amount of sodium silicate stored in a container; and a premeasured amount of a liquid blend consisting essentially of benzotriazole or tolyltriazole and a water soluble surfactant stored in a container; wherein at the time of use said premeasured amount of sodium perborate, said premeasured amount of sodium silicate, and said premeasured amount of the liquid blend are combined with a premeasured amount of water to form an aqueous solution consisting essentially of:
   (a) from about 0.1 to 3.0 percent by weight of at least one alkali metal perborate;
   (b) from about 0.05 to 5.0 percent by weight of at least one alkali metal silicate;
   (c) benzotriazole, tolyltriazole, or a mixture thereof; and
   (d) 0.1 to 5.0 percent by weight of at least one water soluble surfactant;
wherein the composition has a pH ranging from 7.0 to 10, does not include a chlorine bleach, and the combined amount of ingredients (b) and (c) does not exceed about 5.0 weight percent of the composition.

3. The kit of claim 1 wherein the liquid blend is a combination of a cationic surfactant and benzotriazole.

4. The kit of claim 3, wherein the liquid blend is prepared by heating water up to about 120° F., adding the surfactant to the heated water, mixing the water and the surfactant and then adding the benzotriazole.

5. The kit of claim 3 wherein the liquid blend is prepared by heating about 900 ml of distilled water to about 120° F., adding about 60 to 90 grams of the surfactant to the heated water with mixing and subsequently mixing about 40 to 60 grams of benzotriazole with the water and surfactant.

6. The kit of claim 1 wherein the kit comprises a mixing container for mixing the premeasured amount of perborate, the premeasured amount of silicate, the premeasured amount of liquid blend and the premeasured amount of water.

7. The kit of claim 6 wherein the kit includes an agitator for mixing the aqueous solution.

8. The kit of claim 6 wherein the kit includes a storage sleeve for storing the perborate container, the silicate container, and the liquid blend container.

9. The kit of claim 8 wherein the kit includes an agitator for mixing the aqueous solution, said agitator stored within the storage sleeve.

10. A corrosion-inhibiting mildew remover kit consisting essentially of a premeasured amount of powdered sodium perborate stored in a container; a premeasured amount of sodium silicate stored in a container; a premeasured amount of a liquid blend consisting of benzotriazole and tolyltriazole and a premeasured amount of surfactant selected from the group consisting of alkylaryl polyether alcohols, and alkyl polyether alcohols stored in a container; and a container with an agitator for mixing said ingredients; wherein at the time of use said premeasured amount of the sodium perborate, said premeasured amount of the sodium silicate, said premeasured amount of the liquid blend, and said premeasured amount of surfactant are combined with a premeasured amount of water to form an aqueous solution consisting essentially of:
   (a) from about 0.1 to 3.0 percent by weight of sodium perborate;
   (b) from about 0.05 to 5.0 percent by weight of sodium silicate;
   (c) benzotriazole and tolyltriazole; and
   (d) 0.1 to 5.0 percent by weight of said surfactant;
wherein the composition has a pH ranging from 7.0 to 10, does not include a chlorine bleach, and the combined amount of sodium silicate, benzotriazole, and tolyltriazole does not exceed about 5.0 weight percent of the composition.

11. The kit of claim 10 wherein the liquid blend is prepared by heating water up to approximately 120° F., then adding the surfactant to the heated water, mixing the water and the surfactant, and then adding the benzotriazole and tolyltriazole.

12. The kit of claim 11 wherein the kit further contains a set of instructions on the process for using the kit to remove mildew.

* * * * *